United States Patent
Haas et al.

(10) Patent No.: US 7,807,104 B2
(45) Date of Patent: Oct. 5, 2010

(54) INSPECTION TESTER FOR EXPLOSIVES

(75) Inventors: Jeffrey S. Haas, San Ramon, CA (US); Randall L. Simpson, Livermore, CA (US); Joe H. Satcher, Patterson, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 521 days.

(21) Appl. No.: 11/179,436

(22) Filed: Jul. 11, 2005

(65) Prior Publication Data
US 2007/0003435 A1 Jan. 4, 2007

Related U.S. Application Data

(62) Division of application No. 10/610,904, filed on Jun. 30, 2003, now Pat. No. 7,294,306.

(51) Int. Cl.
*G01N 33/00* (2006.01)

(52) U.S. Cl. .............................. 422/58; 422/50; 422/55; 422/68.1; 422/99; 422/103; 436/174; 436/180

(58) Field of Classification Search ................ 436/174, 436/180; 422/50, 55–58, 68.1, 99–103
See application file for complete search history.

(56) References Cited

U.S. PATENT DOCUMENTS

| | | | |
|---|---|---|---|
| 4,554,133 A | 11/1985 | Leichnitz | |
| 4,783,316 A | 11/1988 | Pannwitz | |
| 5,035,862 A * | 7/1991 | Dietze et al. | ............... 422/68.1 |
| 5,310,681 A | 5/1994 | Rounbehler et al. | |
| 5,551,278 A | 9/1996 | Rounbehler et al. | |
| 5,638,166 A | 6/1997 | Funsten et al. | |
| 5,648,047 A * | 7/1997 | Kardish et al. | ................ 422/56 |
| 5,679,584 A | 10/1997 | Mileaf et al. | |
| 5,912,466 A | 6/1999 | Funsten et al. | |
| 6,245,576 B1 | 6/2001 | Hiley | |
| 6,406,918 B1 | 6/2002 | Bannister et al. | |
| 6,470,730 B1 | 10/2002 | Chamberlain | |
| 6,477,907 B1 | 11/2002 | Chambers et al. | |

FOREIGN PATENT DOCUMENTS

| | | |
|---|---|---|
| EP | 0 384 504 A | 8/1990 |
| WO | WO 97/37212 A1 | 10/1997 |

OTHER PUBLICATIONS

Jenkins, T., et al., "Development of Field Screening Methods for TNT, 2,4-DNT and RDX in Soil," Geological Sci., Talonia, vol. 39, No. 4, pp. 419-428, Pergamon Press, 1992.
Hiley, R., "Investigations of Thin Layer Chromatographic Techniques Used for Forensic Explosives Analysis in the Early 1970s," Hiley—TLC Techniques for Explosives Analysis, Journal of Forensic Sciences, Jul. 1993, pp. 864-873.

* cited by examiner

*Primary Examiner*—Sam P Siefke
(74) *Attorney, Agent, or Firm*—Eddie E. Scott; John H. Lee

(57) ABSTRACT

An inspection tester that can be used anywhere as a primary screening tool by non-technical personnel to determine whether a surface contains explosives. It includes a body with a sample pad. First and second explosives detecting reagent holders and dispensers are operatively connected to the body and the sample pad. The first and second explosives detecting reagent holders and dispensers are positioned to deliver the explosives detecting reagents to the sample pad. A is heater operatively connected to the sample pad.

5 Claims, 3 Drawing Sheets

INSPECTION TESTER FOR EXPLOSIVES

CROSS-REFERENCE TO RELATED APPLICATIONS

This application is a division of application Ser. No. 10/610,904 filed Jun. 30, 2003 now U.S. Pat. No. 7,294,306 entitled "Inspection Tester for Explosives."

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to testing and more particularly to an inspection tester for explosives.

2. State of Technology

U.S. Pat. No. 5,638,166 for an apparatus and method for rapid detection of explosives residue from the deflagration signature thereof issued Jun. 10, 1997 to Herbert O. Funsten and David J. McComas and assigned to The Regents of the University of California provides the following state of the art information, "Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. See, Fetterolf et al., Portable Instrumentation: New Weapons in the War Against Drugs and Terrorism," Proc. SPIE 2092 (1993) 40, Yinon and Zitrin, in Modern Methods and Applications in Analysis of Explosions, (Wiley, New York, 1993) Chap. 6; and references therein. Vapor detection is achieved using trained animals, gas chromatography, ion mobility mass spectrometry, and bioluminescence, as examples. All of these techniques suffer from the inherently low vapor pressures of most explosives. Bulk detection of explosives may be performed using x-ray imaging which cannot detect the explosives themselves, but rather detects metallic device components. Another method for bulk detection involves using energetic x-rays to activate nitrogen atoms in the explosives, thereby generating positrons which are detected. This technique requires an x-ray generator and a minimum of several hundred grams of explosives. Bulk detection is also accomplished using thermal neutron activation which requires a source of neutrons and a .gamma.-radiation detector. Thus, bulk detection is not sensitive to trace quantities of explosives and requires large, expensive instrumentation. Tagging requires that all explosives be tagged with, for example, an easily detected vapor. However, since tagging is not mandatory in the United States, this procedure is clearly not reliable. It turns out that there are no technologies for performing accurate, real-time (<6 sec) detection and analysis of trace explosives in situ. Only trained dogs can achieve this goal.

It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," J. Forensic Science 27 (1982) 783; J. D. Twibell et al., "The Persistence of Military Explosives on Hands," J. Forensic Science 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives.

U.S. Pat. No. 5,679,584 for a method for chemical detection issued Oct. 2, 1997 to Daryl Sunny Mileaf and Noe Esau Rodriquez, II provides the following state of the art information, "a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction."

U.S. Pat. No. 6,470,730 for a dry transfer method for the preparation of explosives test samples issued Oct. 29, 2002 to Robert T. Chamberlain and assigned to The United States of America as represented by the Secretary of Transportation provides the following state of the art information, "method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an inspection tester. The inspection tester can be used anywhere as a primary screening tool by non-technical personnel to determine whether a surface contains explosives. The inspection tester comprises a body with a sample pad operatively connected to the body. A first reagent holder and dispenser is operatively connected to the body and the sample pad. The first reagent holder and dispenser contains a first explosives detecting reagent (reagent A) and is positioned to deliver the first explosives detecting reagent to the sample pad. A second reagent holder and dispenser is operatively connected to the body and the sample pad. The second reagent holder and dispenser contains a second explosives detecting reagent (reagent B) and is positioned to deliver the second explosives detecting reagent to the sample pad. A heater is operatively connected to the sample pad.

The inspection tester uses a simple and rapid method of operation. The sample pad is exposed to a suspect substance. This may be accomplished by the sample pad being swiped across a surface containing the suspect substance or the pad may be exposed to the suspect substance in other ways such as adding the suspect substance to the sample pad. The first reagent activation unit is activated depositing the first reagent (reagent A) onto the sample pad with the suspect substance. If the sample pad becomes colored, it's positive for explosives. If no color appears then the additional steps are performed. In the next step, the heater is activated. If a color appears on the sample pad, the test positive for explosives. If no color appears then the additional step is performed. In the next step, the second reagent activation unit is activated depositing the second reagent (reagent B) onto the sample pad with the suspect substance. If the sample pad becomes colored, the test is positive for explosives. If no color appears then the test is negative for explosives.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
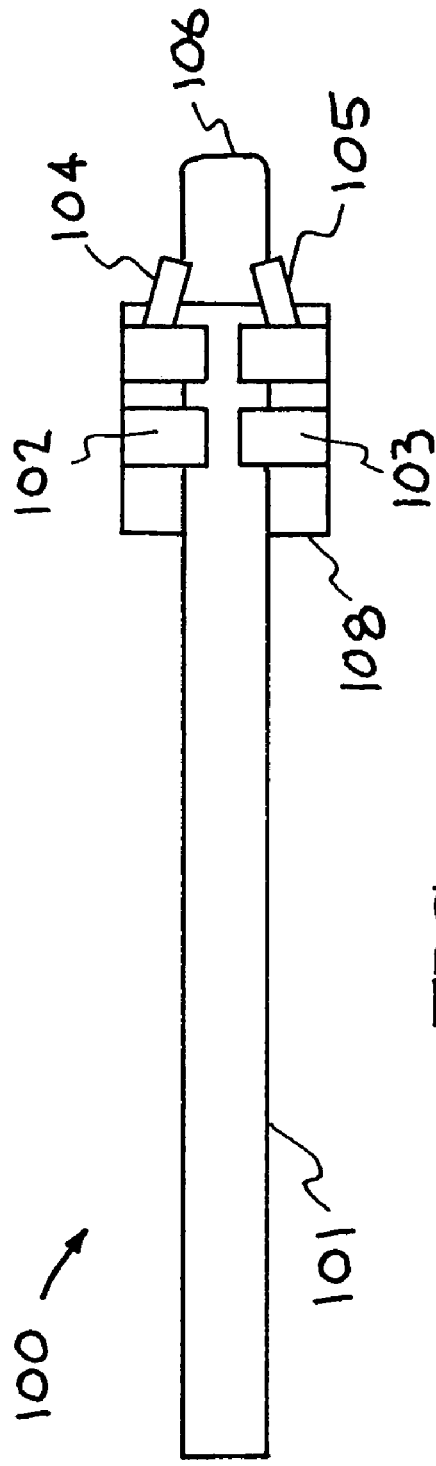
FIG. 1 illustrates a top view of one embodiment of an inspection tester for explosives constructed in accordance with the present invention.

Referring now to the drawings and the following detailed description, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 2:
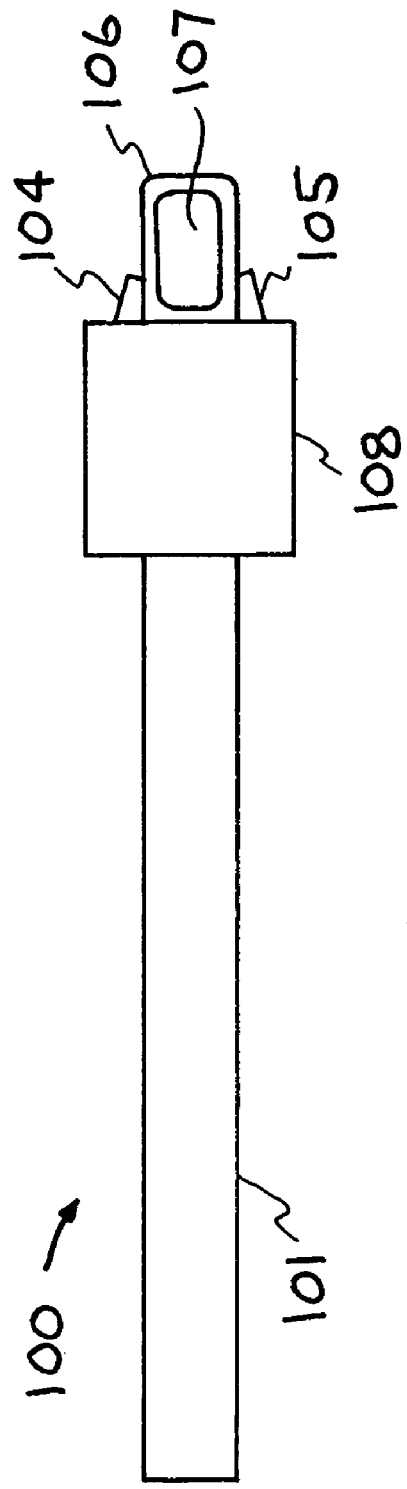
FIG. 2 is a bottom view of the embodiment of the inspection tester for explosives illustrated in FIG. 1.

Referring now to FIGS. 1 and 2 of the drawings, a top view and a bottom view of one embodiment of an inspection tester for explosives constructed in accordance with the present invention is illustrated. This embodiment of the present invention is designated generally by the reference numeral 100. The inspection tester 100 is an all-inclusive, inexpensive, and disposable device.

The inspection tester 100 comprises a sample collection unit 106 attached to body section 101. Two reagent activation units, activation unit 102 (for reagent A) and activation unit 103 (for reagent B), are operatively connected to the body 101. Two reagent holders, reagent holder 104 (reagent A) and reagent holder 105 (reagent B) are operatively connected to the sample collection unit 106 and the reagent activation units 102 and 103. A heater 107 is operatively connected to the sample collection unit 106.

The structural details of embodiment of an inspection tester for explosives constructed in accordance with the present invention having been described the operation of the inspection tester 100 will now be considered. The inspection tester 100 uses a simple and rapid procedure summarized by the following four step operation:

Step #1—The sample collection unit 106 is exposed to the suspect substance. This may be accomplished by the sample collection unit 106 being swiped across a surface containing the suspect substance or the sample collection unit 106 may be exposed to the suspect substance in other ways such as adding the suspect substance to the sample collection unit 106.

Step #2—The reagent activation unit 102 (for reagent A) is activated depositing reagent A from reagent holder 104 onto the sample collection unit 106 with the suspect substance. If the sample collection unit 106 becomes colored, it's positive for explosives. If no color appears then the additional steps are performed.

Step #3—The heater 107 is activated. If a color appears on the sample collection unit 106, it's positive for explosives. If no color appears then the additional step is performed.

Step #4—The reagent activation unit 103 (for reagent B) is activated depositing reagent B from reagent holder 105 onto the sample collection unit 106 with the suspect substance. If the sample collection unit 106 becomes colored, it's positive for explosives. If no color appears then the test is negative for explosives.

The particular embodiment of the inspection tester 100 has detection limits between 0.1 to 100 nanograms, depending on the type of explosives present. The chemistry reaction scheme, the types of chemicals, the concentrations, the quantity, and the heat, have been optimized to provide the best results. A large number of common military and industrial explosives can be easily detected such as HMX, RDX, NG, TATB, Tetryl, PETN, TNT, DNT, TNB, DNB and NC. Many more compounds are being added to this list.

The inspection tester 100 is extremely fast, sensitive, very easy to implement, and has virtually no false positives. The inspection tester 100 is inexpensive and disposable. The inspection tester 100 can be used virtually anywhere, car portal checkpoints, airports, first responders, Federal, State, and local agencies. The inspection tester 100 can be used as a primary screening tool by non technical personnel to determine whether a surface contains explosives. Explosive Ordinance Disposal teams cannot simply explode suspect packages for concerns of disbursing radioactive material, biological agents, or chemical agents.

The particular embodiment of an inspection tester 100 will now be described in greater detail. As shown in FIG. 1 a swab 106 is attached to one end of a pencil sized wand 101. The other end of the wand 101 serves as a handle. The swab 106 can be made of cotton, paper, polymer, or various other materials that will serve to retain and/or collect a sample. The wand 101 can be made of plastic, wood, metal, or various other materials. The swab 106 is attached to the wand 101 by any suitable means such as glue, heating, crimping or various other means of attachment.

Two slider buttons, slider button A and slider button B, are positioned to slide axially along the wand 101. The slider button A is designated by the reference numeral 102 and the slider button B is designated by the reference numeral 103. The slider button A and slider button B are held in sliding engagement relative to wand 101 by a retainer 108 attached to wand 101. A reagent holder A is positioned along wand 101 between slider button A and swab 106. A reagent holder B is positioned along wand 101 between slider button A and swab 106. The reagent holder A is designated by the reference numeral 104 and the reagent holder B is designated by the reference numeral 105. The reagent in reagent holder A contains Meisenheimer complexes. The reagent in reagent holder B provides a Griess reaction. The Meisenheimer complexes and Griess reaction are well known in the art and need not be described here.

FIG. 2 shows a bottom view of the inspection tester 100. The bottom of the retainer 108, the reagent holder A, and the reagent holder B are shown near the end of the wand 101. A heater 107 is attached to the end of the wand 101. The heater is located beneath the swab 106 and in contact with the swab 106. The heater 107 is a chemical heater. This type of heater is well known in the art and need not be described here. Other type of heaters such as electrical heaters can be used for heater 107.

Operation of the inspection tester 100 can be described according to the following simple four-step process:

STEP 1) A suspect surface is swiped with the swab 106. This will cause any explosives residue to be colleted and held by the swab 106.

STEP 2) The slider button A, reference numeral 102, is pressed so that slider button A moves along the wand 101 toward swab 106. This causes the reagent holder A, reference numeral 104, to be moved into contact with swab 106. The regent A in reagent holder A is deposited on the swab 106 and contacts any explosives residue that has been collected by swab 106. If the swab 107 becomes colored, the test is positive for explosives. If no color appears the test for explosives is negative.

STEP 3) The heater 107 is activated. This causes the swab 107, reagent A, and any explosives residue to become heated. If the swab 107 now becomes colored, the test is positive for explosives. If no color appears the test for explosives is negative.

STEP 4) The slider button B, reference numeral 103, is pressed so that slider button B moves along the wand 101 toward swab 106. This causes the reagent holder B, reference numeral 103, to be moved into contact with swab 106. The regent B in reagent holder B is deposited on the swab 106 and contacts any explosives residue that has been collected by swab 106. If the swab 107 becomes colored, the test is positive for explosives. If no color appears the test for explosives is negative.

The operation of the inspection tester for explosives 100 is extremely fast, sensitive, low-cost, very easy to implement, and has virtually no false positives. The operation describe above takes approximately 15 seconds. In practice, the inspection tester for explosives 100 can be used anywhere as a primary screening tool by non technical personnel to determine whether a surface contains explosives. The inspection tester for explosives 100 has many important uses. For example, explosive ordinance disposal teams cannot simply explode suspect packages for concerns of disbursing radioactive material, biological agents, or chemical agents. The inspection tester for explosives 100 provides a fast, sensitive, low-cost, very easy to implement system for testing the suspected packages. The inspection tester for explosives 100 is inexpensive and disposable.

The inspection testers 100 can be stored and carried in a test kit that would contain hundreds of the disposable inspection tester for explosives 100. The inspection tester for explosives 100 can be used virtually anywhere, car portal checkpoints, airports, first responders, Federal, State, and local agencies. The inspection tester for explosives 100 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC.

Figure 3:
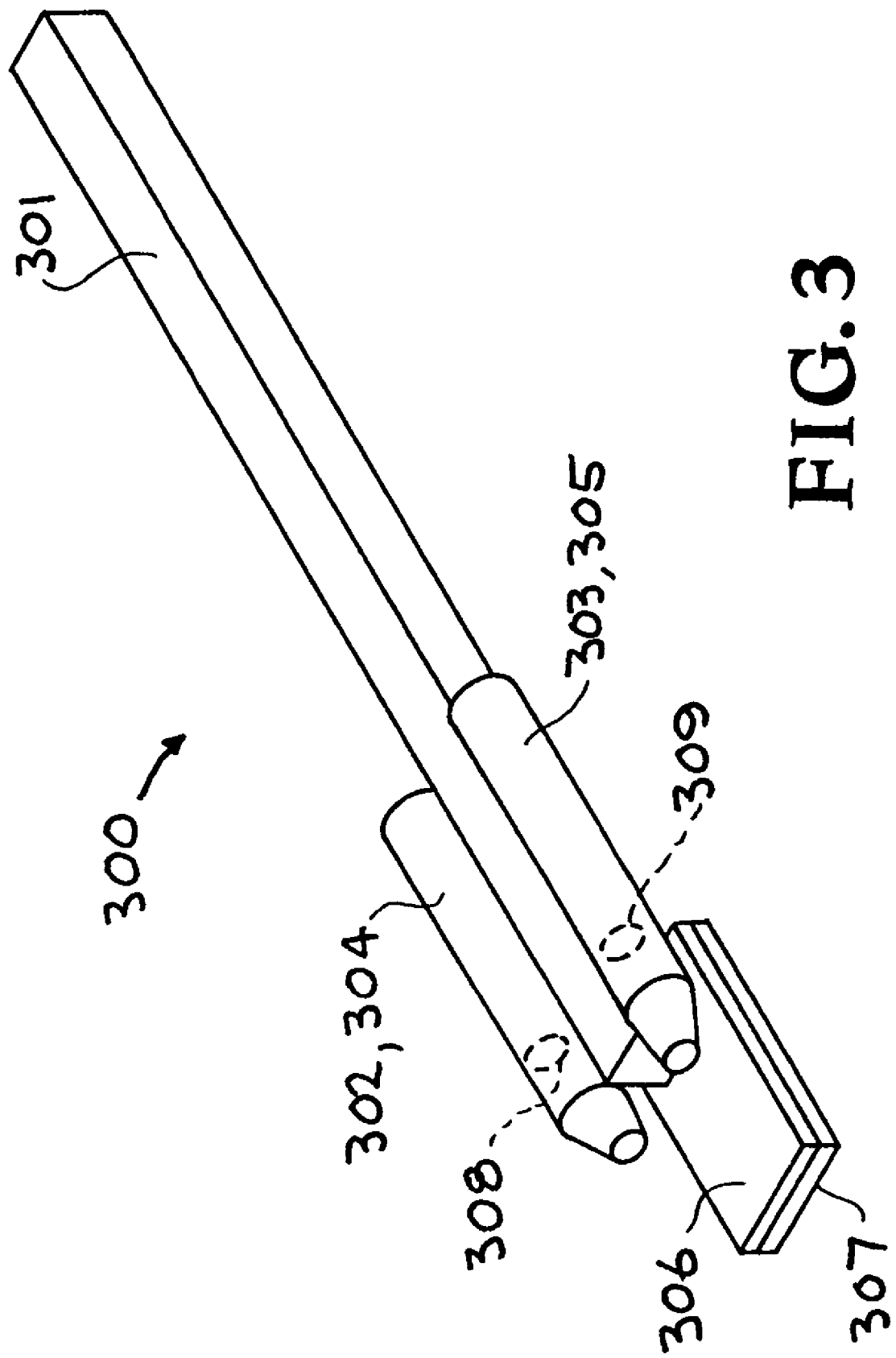
FIG. 3 illustrates another embodiment of an inspection tester for explosives constructed in accordance with the present invention.

Referring now to FIG. 3 another embodiment of an inspection tester for explosives constructed in accordance with the present invention is illustrated. This embodiment is designated generally by the reference numeral 300. The inspection tester 300 comprises a body 303 with a sample pad 306 operatively connected to the body 301. A first explosives detecting reagent 304 is contained in a first reagent holder and dispenser 302 that is operatively connected to the body 301 and the sample pad 306. The first reagent holder and dispenser 301 containing the first explosives detecting reagent 304 is positioned to deliver the first explosives detecting reagent 304 to the sample pad 306. A second explosives detecting reagent 305 is contained in a second reagent holder and dispenser 303 operatively connected to the body 301 and the sample pad 306. The second reagent holder and dispenser 303 containing the second explosives detecting reagent 305 is positioned to deliver the second explosives detecting reagent 303 to the sample pad 306. A heater 307 is operatively connected to the sample pad 306.

The sample pad in the embodiment 300 comprises a swab 306 that is attached to one end of an elongated wand 301. The other end of the wand 301 serves as a handle. The swab 306 can be made of cotton, paper, polymer, or various other materials that will serve to retain and/or collect a sample. The wand 301 can be made of plastic, wood, metal, or various other materials. The swab 306 is attached to the wand 301 by any suitable means such as glue, heating, crimping or various other means of attachment.

The first reagent holder and dispenser 302 contains the first explosives detecting reagent 304 (reagent A) and the second reagent holder and dispenser 303 contains the second explosives detecting reagent 305 (reagent B). The reagent A contains Meisenheimer complexes. The reagent B provides a Griess reaction. The Meisenheimer complexes and Griess reaction are well known in the art and need not be described here.

The first reagent holder and dispenser 302 is positioned to deliver the first explosives detecting reagent (reagent A) 304 to the swab 306. The second reagent holder and dispenser 303 is positioned to deliver the second explosives detecting reagent (reagent B) 305 to the swab 306. The first and second reagent holders and dispensers 302 and 303 are squeezable vials with internal valves 308 and 309 respectively that deliver the first explosives detecting reagent (reagent A) 304 and the second explosives detecting reagent (reagent B) 305 to the swab 306. This type of squeezable vial is well know in the art and is readily availed for purchase from many suppliers.

The heater 307 is attached to the end of the wand 301. The heater is located beneath the swab 306 and in contact with the swab 306. The heater 307 is a chemical heater. This type of heater is well known in the art and need not be described here. Other type of heaters such as electrical heaters can be used for heater 307.

The structural details of embodiment of an inspection tester for explosives constructed in accordance with the present invention having been described the operation of the inspection tester 300 will now be considered. The inspection tester 300 uses a simple and rapid procedure summarized by the following four step operation:

STEP 1) A suspect surface is swiped with the swab 306. This will cause any explosives residue to be colleted and held by the swab 306.

STEP 2) The squeezable vial 302 is pressed dispensing reagent A 304 through internal valve 308 onto swab 306. The regent A 304 contacts any explosives residue that has been collected by swab 306. If the swab 307 becomes colored, the test is positive for explosives. If no color appears the test for explosives is negative to this point.

STEP 3) The heater 307 is activated. This causes the swab 307, reagent A 304, and any explosives residue to become heated. If the swab 307 now becomes colored, the test is positive for explosives. If no color appears the test for explosives is negative to this point.

STEP 4) The squeezable vial 303 is pressed dispensing reagent B 305 through internal valve 309 onto swab 306. The regent B 305 contacts any explosives residue that has been collected by swab 306. If the swab 307 becomes colored, the test is positive for explosives. If no color appears the test for explosives is negative.

The inspection tester for explosives 300 provides a fast, sensitive, low-cost, very easy to implement system for testing the suspected packages. The inspection tester for explosives 300 is inexpensive and disposable.

The inspection testers 300 can be stored and carried in a test kit that would contain hundreds of the disposable inspection tester for explosives 300. The inspection tester for explosives 300 can be used virtually anywhere, car portal checkpoints, airports, first responders, Federal, State, and local agencies. The inspection tester for explosives 300 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC.

Figure 4:
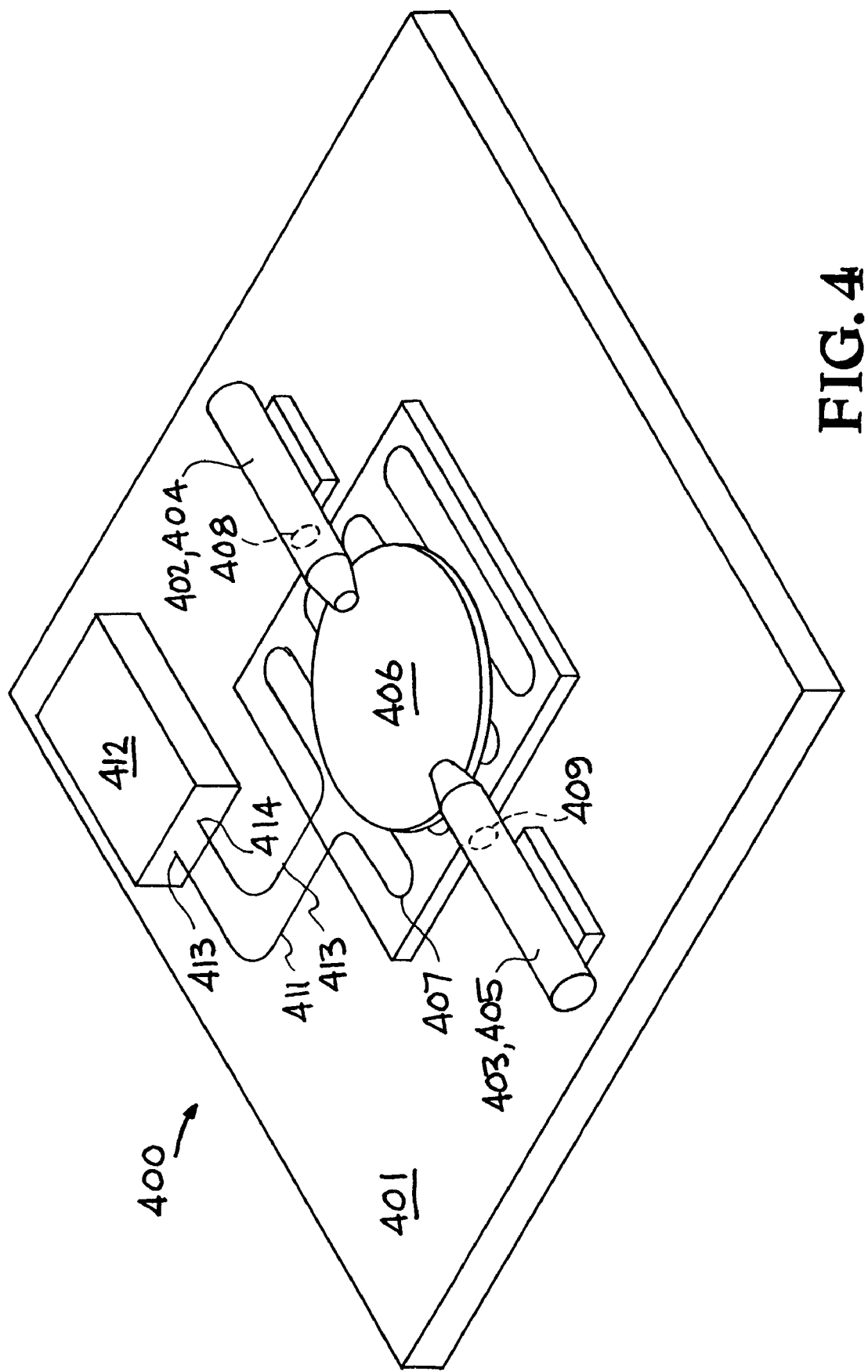
FIG. 4 illustrates yet another embodiment of an inspection tester for explosives constructed in accordance with the present invention.

Referring now to FIG. 4 yet another embodiment of an inspection tester for explosives constructed in accordance with the present invention is illustrated. This further embodiment is designated generally by the reference numeral 400. The inspection tester 400 comprises a body 401 with a sample pad 406 operatively connected to the body 401. A first explosives detecting reagent 404 (reagent A) is contained in a first reagent holder and dispenser 402 that is operatively connected to the body 401 and the sample pad 406. The first reagent holder and dispenser 402 containing the first explosives detecting reagent 404 is positioned to deliver the first explosives detecting reagent 404 to the sample pad 406. A second explosives detecting reagent 405 (reagent B) is contained in a second reagent holder and dispenser 403 operatively connected to the body 401 and the sample pad 406. The second reagent holder and dispenser 403 containing the second explosives detecting reagent 405 is positioned to deliver the second explosives detecting reagent 403 to the sample pad 406. A heater 407 is operatively connected to the sample pad 406.

The sample pad in the embodiment 400 comprises a disk shaped cotton pad 406 that is attached to the body 401. The pad 406 can be made of cotton, paper, polymer, or various other materials that will serve to retain and/or collect a sample. The body 401 can be made of polymer, plastic, wood, metal, or various other materials. The pad 406 is attached to the body 401 by any suitable means such as thermoset, glue, or various other means of attachment.

The first reagent holder and dispenser 402 contains the first explosives detecting reagent 404 (reagent A) and the second reagent holder and dispenser 403 contains the second explosives detecting reagent 405 (reagent B). The reagent A contains Meisenheimer complexes. The reagent B provides a Griess reaction. The Meisenheimer complexes and Griess reaction are well known in the art and need not be described here.

The first reagent holder and dispenser 402 is positioned to deliver the first explosives detecting reagent (reagent A) 404 to the pad 406. The second reagent holder and dispenser 403 is positioned to deliver the second explosives detecting reagent (reagent B) 405 to the pad 406. The first and second reagent holders and dispensers 402 and 403 are squeezable vials with internal valves 408 and 409 respectively that deliver the first explosives detecting reagent (reagent A) 404 and the second explosives detecting reagent (reagent B) 405 to the pad 406. This type of squeezable vial is well know in the art and is readily availed for purchase from many suppliers.

The heater 407 is located beneath the pad 406 and in contact with the pad 406. The heater 407 is an electrical heater with a heating element extending in zig zag arrangements and electrical leads 410 and 411. The electrical leads 410 and 411 can be connected to an external battery 412 with corresponding lead holes 413 and 414. Other types of heaters can be used for the heater 407, such as chemical heaters.

The structural details of embodiment of an inspection tester for explosives constructed in accordance with the present invention having been described the operation of the inspection tester 400 will now be considered. The inspection tester 400 uses a simple and rapid procedure summarized by the following four step operation:

STEP 1) A suspect surface is swiped with the pad 406. This will cause any explosives residue to be colleted and held by the pad 406.

STEP 2) The squeezable vial 402 is pressed dispensing reagent A 404 through internal valve 408 onto pad 406. The regent A 404 contacts any explosives residue that has been collected by pad 406. If the pad 407 becomes colored, the test is positive for explosives. If no color appears the test for explosives is negative to this point.

STEP 3) The heater 407 is activated. This causes the pad 407, reagent A 404, and any explosives residue to become heated. If the pad 407 now becomes colored, the test is positive for explosives. If no color appears the test for explosives is negative to this point.

STEP 4) The squeezable vial 403 is pressed dispensing reagent B 405 through internal valve 409 onto pad 406. The regent B 405 contacts any explosives residue that has been collected by pad 406. If the pad 407 becomes colored, the test is positive for explosives. If no color appears the test for explosives is negative.

In one use of the inspection tester 400 provides a simple, chemical, field spot-test by to provide a rapid screen for the presence of a broad range of explosive residues. The inspection tester 400 is fast, extremely sensitive, low-cost, very easy to implement, and provides a very low rate of false positives. The inspection tester for explosives 400 provides a fast, sensitive, low-cost, very easy to implement system for testing the suspected packages. The inspection tester for explosives 400 is inexpensive and disposable. The inspection tester for explosives 400 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 400 is small enough that a number of them can fit in a pocket or brief case.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of testing an object for explosives by determining whether a color appears indicating the presence of explosives, comprising the following steps in the following order:

swiping the object with a sample pad, providing a first reagent for detecting explosives, delivering said first reagent to said sample pad, if color appears it indicates the presence of explosives, if no color appears the next step is performed, heating said sample pad, viewing said sample pad to observe any color change in said sample pad, if color appears it indicates the presence of explosives, if no color appears the next step is performed, providing a second reagent for detecting explosives, delivering said second reagent to said sample pad, if color appears it indicates the presence of explosives, if no color appears the next step is performed, heating said sample pad, and viewing said sample pad to observe any color change in said sample pad, if color appears it indicates the presence of explosives, if no color appears the test is negative for explosives.

2. A method for detecting the presence of explosive elements by determining whether a color appears indicating the presence of explosives comprising the following steps in the following order:

swiping an object to obtain a test sample using a sample element having a swipe pad;

placing said sample element in a sample holder in a testing device and retaining said sample element with a sample retainer;

applying a first reagent fluid from a fluid retainer on said swipe pad, if color appears it indicates the presence of explosives, if no color appears the next step is performed;

activating a heater disposed under said sample element; heating said swipe pad to a temperature to activate said first reagent fluid with said test sample;

viewing said swipe pad to observe any color change in said test sample, if color appears it indicates the presence of explosives, if no color appears the next step is performed;

applying a second reagent fluid from a second fluid retainer on said swipe pad; and viewing said swipe pad to observe any color change in said test sample, if color appears it indicates the presence of explosives.

3. The method for detecting the presence of explosive elements of claim 2 wherein said first reagent fluid comprises Meisenheimer complexes.

4. The method for detecting the presence of explosive elements of claim 2 wherein said second reagent fluid provides a Griess reaction.

5. The method for detecting the presence of explosive elements of claim 2 including the following steps:

if no color appears after applying a second reagent fluid from a second fluid retainer, activating a heater disposed under said sample element; heating said swipe pad to a temperature to activate said second reagent fluid with said test sample; and viewing said sample pad to observe any color change in said sample pad, if color appears it indicates the presence of explosives, if no color appears the test is negative for explosives.

* * * * *